United States Patent
Parachur et al.

(10) Patent No.: US 10,792,252 B2
(45) Date of Patent: Oct. 6, 2020

(54) HIGHLY CONCENTRATED POWDERED OLEORESIN COMPOSITION AND PROCESS FOR PREPARATION THEREOF

(71) Applicant: Vivek Anand Parachur, Chennai (IN)

(72) Inventors: Vivek Anand Parachur, Chennai (IN); Sripathy Ravichandran, Chennai (IN); Sanjib Kumar Panda, Chennai (IN)

(73) Assignee: Vivek Anand Parachur, Chennai (IN)

( * ) Notice: Subject to any disclaimer, the term of this patent is extended or adjusted under 35 U.S.C. 154(b) by 289 days.

(21) Appl. No.: 15/574,410

(22) PCT Filed: May 14, 2016

(86) PCT No.: PCT/IN2016/050139
§ 371 (c)(1),
(2) Date: Nov. 15, 2017

(87) PCT Pub. No.: WO2016/185488
PCT Pub. Date: Nov. 24, 2016

(65) Prior Publication Data
US 2018/0289622 A1    Oct. 11, 2018

(30) Foreign Application Priority Data
May 15, 2015 (IN) .......................... 2463/CHE/2015

(51) Int. Cl.

| | | |
|---|---|---|
| *A61K 36/00* | (2006.01) |
| *A61K 9/14* | (2006.01) |
| *A61K 36/81* | (2006.01) |
| *A61K 36/9066* | (2006.01) |
| *A61K 36/9068* | (2006.01) |
| *A61K 36/185* | (2006.01) |
| *A61K 36/28* | (2006.01) |
| *A61K 36/48* | (2006.01) |
| *A23L 33/105* | (2016.01) |
| *A61K 31/12* | (2006.01) |
| *A61P 9/00* | (2006.01) |
| *A61K 36/54* | (2006.01) |

(52) U.S. Cl.
CPC ............ *A61K 9/145* (2013.01); *A23L 33/105* (2016.08); *A61K 9/143* (2013.01); *A61K 9/146* (2013.01); *A61K 31/12* (2013.01); *A61K 36/185* (2013.01); *A61K 36/28* (2013.01); *A61K 36/48* (2013.01); *A61K 36/54* (2013.01); *A61K 36/81* (2013.01); *A61K 36/9066* (2013.01); *A61K 36/9068* (2013.01); *A61P 9/00* (2018.01); *A23V 2002/00* (2013.01)

(58) Field of Classification Search
CPC ..................................................... A61K 36/00
USPC ......................................................... 424/725
See application file for complete search history.

(56) References Cited

U.S. PATENT DOCUMENTS

2003/0228369 A1    12/2003    Kuhrts
2006/0171995 A1    8/2006    Kaw et al.
2017/0258912 A1*   9/2017    Odidi ................... A61K 9/2813

* cited by examiner

*Primary Examiner* — Michael V Meller
(74) *Attorney, Agent, or Firm* — Kramer Amado, P.C.

(57) ABSTRACT

The invention disclosed herein is a highly concentrated powdered oleoresin composition comprises oleoresin(s), Mineral hydroxide(s)/oxide(s)/chloride(s)/carbonate(s) and optionally comprises organic/inorganic acid(s); wherein said composition has enhanced stability and increased bioavailability. The invention also disclosed herein a process for preparation of said composition.

2 Claims, 2 Drawing Sheets

HIGHLY CONCENTRATED POWDERED OLEORESIN COMPOSITION AND PROCESS FOR PREPARATION THEREOF

TECHNICAL FIELD OF THE INVENTION

The present invention relates to a highly concentrated powdered oleoresin composition and process for preparation thereof.

BACKGROUND OF THE INVENTION

Oleoresins are extracted from the spices that reproduce the character of the respective spice. Oleoresins are the extracts obtained by solvent extraction of ground spices. They have a wide range of applications in food, nutraceutical and pharmaceutical industries. India is one of the leading producers of spices. With increasing preference for quality products, use of spices is rapidly replaced with oleoresins and spice oils. Export of these processed products, instead of raw spices, would also result in considerable value addition. Oleoresins are more economical than whole or ground spices as the same effect can be obtained using less quantity of the desired material.

Oleoresins are more preferred over raw spice for several economically important properties. Some of those properties include, but not limited to, microbiological advantages, uniformity in flavour and pungency, easy to store and transport over spice powders. Spice oleoresins are widely used for flavoring of food particularly by large scale food processing and flavoring industries like meat canning, sauces, soft drinks, pharmaceutical preparations, nutraceutical preparations, veterinary preparations, perfumery and soap, tobacco, confectionery and baking industries.

Oleoresines are manufactured by solvent extraction of spice using several solvents and then distillation, resulting in viscous liquid oleoresins.

Currently oleoresins are available primarily in the form of liquid. Oleoresins in liquid forms have various disadvantages/drawbacks. Major drawbacks are its stability and its limitations in use as direct ingredients in powder formulations due to it being a highly viscous liquid. Due to their high viscosity, it is very difficult to handle the liquid oleoresins during manufacturing of products containing oleoresins. Also it is difficult to ensure the uniformity of liquid oleoresins in the powdered finished product due to their higher viscosity. There is a chance of formation of lumps in the powder formulation, which are difficult to handle during the manufacturing. This may also lead to quality problems. Oleoresins are less stable in liquid form and will have stability ranging from 3 months to 12 months. Liquid oleoresins also limit their capsulation for various pharmaceutical and nutraceutical applications. In many instances, they have to be converted into powder form before such use. Thus to alleviate all these problems, powder forms of oleoresins are gaining importance.

There are few methods currently adopted to convert liquid Oleoresins into powder.
- A. Conventionally, the oleoresins are mixed with/loaded onto dry carriers to convert it to powder form.
- B. Microencapsulation is another method being used for converting oleoresins into powder. Microencapsulation is known to enhance the stability of Oleoresins by preserving volatile oil and also amicable to add into powder formulation. This can be directly capsulated and used in pharmaceutical or nutraceutical products. It is also useful in powder blending and in the process or formulations, where powdered ingredients are useful.
- C. Spray drying along with maltodextrin or gum arabica is one more method to get the powdered oleoresins.

However, the maximum concentration of the oleoresins in the finished powder product from the above methods is below 30%. Due to the dilution/low oleoresin concentration, dose volume increases which limit its use in many applications, such as nutraceutical and pharmaceutical formulations, resulting into poor bioavailability.

Currently there are no Oleoresin products in powdered form with higher concentration (>30%) of Oleoresins. Thus, there is a need for highly concentrated oleoresins in powder form, which will solve many of the problems associated with formulations containing liquid oleoresins.

SUMMARY OF THE INVENTION

Accordingly in an aspect, the current invention provides a highly concentrated powdered oleoresin composition which has enhanced stability and increased bioavailability.

In another aspect, the invention provides a highly concentrated powdered oleoresin composition comprising Oleoresin(s), organic/inorganic acid(s) and Mineral hydroxide(s)/oxide(s)/chloride(s)/carbonate(s).

In another aspect, the invention provides a highly concentrated powdered oleoresin composition comprising Oleoresin(s) and Mineral hydroxide(s)/oxide(s)/chloride(s)/carbonate(s); wherein said composition is devoid of organic/inorganic acid(s).

In yet another aspect, the invention provides a process for preparation of highly concentrated powdered oleoresin composition.

DETAILED DESCRIPTION OF THE INVENTION

Figure 1:
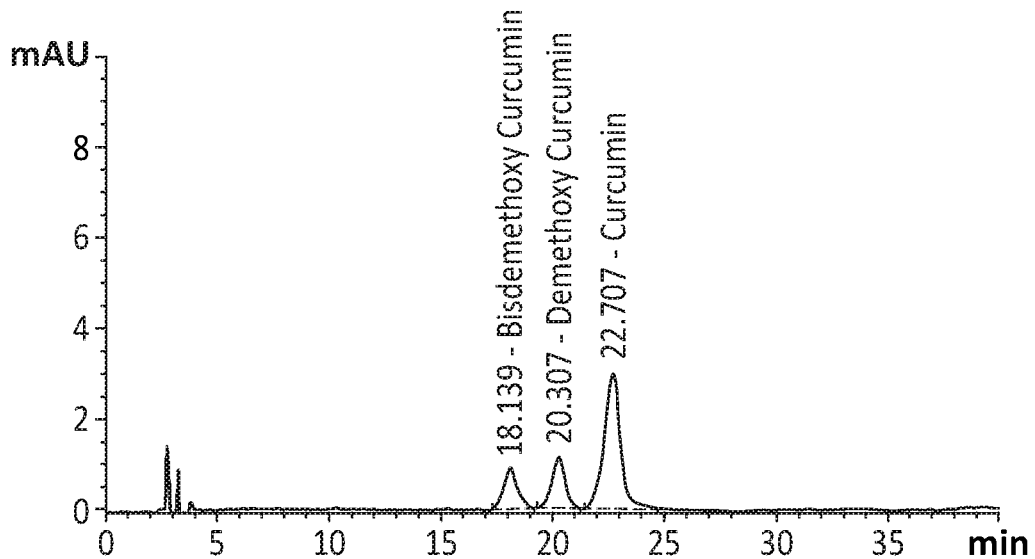
FIG. 1 represents the HPLC chromatogram for Turmeric oleoresin powder of composition of Example 1.

The invention will now be described in detail in connection with certain preferred and optional embodiments, so that various aspects thereof may be more fully understood and appreciated.

Source of the Oleoresins:

Oleoresins can also be extracted using the respective herb or herbal/spice parts using organic solvents, where the herbal part is dried, pulverized into desired particle size and extracted using organic solvent or supercritical $CO_2$. Extraction can be done by percolating the solvents through ground herbal/spice parts in percolator or reactor. This gives rise to liquid or semisolid extract. The Oleoresins, gum resins, resins are commonly available in the market.

Oleoresin(s) used in the present invention are purchased or procured from universal oleoresins and Kancor ingredients ltd.

Abbreviation of Terms

The term "Formulated" as used in the description means composition of the present invention comprising Oleoresins and minerals/acids.

The term "Unformulated" as used in the description means composition comprises only oleoresins.

The present invention discloses a highly concentrated powdered oleoresin composition that has enhanced stability as compared to their respective oleoresins.

Accordingly, in one embodiment, the present invention discloses a highly concentrated powdered oleoresin composition comprises of oleoresin(s), organic/inorganic acid(s) and Mineral hydroxide(s)/oxide(s)/chloride(s)/carbonate(s) having enhanced stability and increased bioavailability.

In another embodiment, the present invention discloses a highly concentrated powdered oleoresin composition comprises of Oleoresin(s) and Mineral hydroxide(s)/oxide(s)/chloride(s)/carbonate(s); wherein said composition is devoid of organic/inorganic acid(s).

The oleoresins includes spice/plant and herbal oleoresins but not limited to Clove Oleoresins, Curry leaf Oleoresins, Pepper Oleoresins, Cardamom Oleoresins, Chilli Oleoresins, Capsicum Oleoresins, Paprika Oleoresins, Ginger Oleoresins, *Curcuma xanthorrhiza* Oleoresins, Turmeric Oleoresins, Coriander Oleoresins, Cumin Oleoresins, Celery Oleoresins, Dill Oleoresins, Fenugreek Oleoresins, Garlic Oleoresins, Mace Oleoresins, Garcinia Extract, Fennel Oleoresins, Tamarind Oleoresins, Cinnamon Oleoresins, Nutmeg Oleoresins, Cassia Oleoresins, Galangal Oleoresins, Parsley Oleoresins, Thyme Oleoresins, Marigold Oleoresins, Rose mary Oleoresins, Mustard Oleoresins, Curry Powder Oleoresins and Vanilla Oleoresins either alone or in combination. The amount of oleoresins present in the composition ranges from 30 to 90%, preferably, 70 to 90%.

The preferred oleoresins includes Turmeric Oleoresin, Marigold oleoresin, Fenugreek oleoresin, Cinnamon oleoresin, Nutmeg oleoresin, Paprika oleoresin, Capsicum oleoresin and Ginger oleoresin, either alone or in combination.

The mineral hydroxide/oxides/chlorides/carbonates are selected from but not limited to calcium hydroxide, Manganese dioxide/oxide, Magnesium hydroxide/magnesium oxide, magnesium chloride, zinc hydroxide/zinc oxide, iron hydroxide/iron oxide and aluminium hydroxide, selenium hydroxide/selenium oxide, sodium hydroxide, potassium hydroxide/potassium oxide wherein, the most preferred being calcium hydroxide and magnesium hydroxide used either alone or in combination. The calcium hydroxide and magnesium hydroxides both are in powder form with the purity ranging from 10 to 99.9% and their concentration in the final composition ranges from 0.01 to 50% and from 0.01 to 50% respectively.

The organic/inorganic acids are selected from Propionic acid, formic acid, acetic acid, Citric acid, butyric acid, valeric acid, caproic acid, oxalic acid, lactic acid, malic acid, benzoic acid, phosphoric acid and carbonic acid either alone or in combination, while the most preferred being Propionic acid. The concentration of organic acids ranges from 0.001 to 20%, preferably, 2 to 6%.

Accordingly, in a preferred embodiment, the invention provides a highly concentrated powdered oleoresin composition which comprises,
a) Oleoresin(s) in an amount of 30 to 90%;
b) organic acid(s) in an amount of 0.001 to 20%; and
c) mineral hydroxide(s) and/or oxide(s)/chloride(s)/carbonate(s) in an amount of 0.01 to 50%.

The invention further provides a highly concentrated powdered oleoresin composition which comprises,
a) Oleoresin(s) in an amount of 30 to 90%; and
b) mineral hydroxide(s) and/or oxide(s)/chloride(s)/carbonate(s) in an amount of 0.01 to 50%.
wherein said composition is devoid of organic/inorganic acid(s).

The highly concentrated powdered oleoresin composition contains 60 to 90% oleoresins and is prepared by reacting oleoresin with calcium and/or magnesium hydroxide powder. Said composition obtained by a unique process, wherein the oleoresins are reacted with calcium and/or magnesium hydroxide under specific temperature range for specified time.

Accordingly, in another preferred embodiment, the invention describes a process for preparation of highly concentrate powdered oleoresin composition, which comprises,
a) Heating sufficient quantity of Oleoresins to the temperature between 25 to 80° C., more specifically 40 to 50° C.;
b) adding organic/inorganic acid to step (a) followed by blending;
c) adding Mineral hydroxide(s)/oxide(s)/chloride(s)/carbonate(s) to step (b) followed by blending/mixing for 5 to 30 minutes; and
d) cooling the mixture of step (c) followed by powdering into free flowing powder.

The invention further describes a process for preparation of highly concentrate powdered oleoresin composition, without use of organic/inorganic acids, which comprises,
a) Heating sufficient quantity of Oleoresins to the temperature between 25 to 80° C., more specifically 40 to 50° C.;
b) adding Mineral hydroxide(s)/oxide(s)/chloride(s)/carbonate(s) to step (a) followed by blending/mixing for 5 to 30 minutes; and
c) cooling the mixture of step (b) followed by powdering into free flowing powder.

In the above mentioned processes precipitated silica/Magnesium stearate can be added optionally.

The obtained composition is a free flowing powder containing >60% oleoresins either alone or in combinations. The composition is highly stable and amicable to blend it with powder formulation with high concentration of oleoresins.

Further, the composition may contain pharmaceutically and nutraceuticaly accepted carriers, excipients, gliding agents, anti-caking agents, binding agents, polymers (natural or synthetic) to increase the flow properties and adjust the final oleoresin concentration.

The said composition with high amount of oleoresin will have higher stability compared to the respective liquid oleoresin and will be amicable for numerous applications, where liquid oleoresins might not be suitable. The liquid Oleoresin is viscous and sticky in nature and hence very difficult to handle during the manufacturing of products containing the same, especially in nutraceutical and pharmaceutical formulations. Also, Liquid Oleoresins are difficult to disperse in formulation matrix due to their high viscosity and similar problem persists while formulating powder formulations. The said highly concentrated form of the powdered Oleoresins can be used for various applications, such as direct capsuling or tableting for nutraceutical and/or pharmaceutical application, food and beverage applications, medicated foods and also can be further formulated with other dry ingredients for human and animal consumption.

The food application includes the use as ingredients in tea bags, coffee bags and other beverages for delivering therapeutically active amount of phytochemicals.

The said composition of the present invention can be further formulated using liposomal technology, emulsion gel technology, permeation enhancers, bioavailability enhancers, coating technologies including enteric coating, reverse enteric coating, taste masking and controlled release technologies.

The highly concentrated powdered oleoresin composition of the present invention can be used for various human and animal health applications such as cardiovascular disease, cognitive disease, gut disease, oral hygiene, eye diseases, skin disease, osteoarthritis, obesity, diabetes, inflammatory disease, respiratory diseases, pain conditions, brain diseases, liver health, kidney health, immune disorders either as drug or nutraceuticals or supplements, as food ingredient, beverage ingredients, feed ingredient and pharmaceutical ingredient.

The highly concentrated powdered oleoresin composition of the present invention can be further formulated into all possible dosage forms such as but not limited to capsules, tablets, sachets, Gummies, Chocolates, candies, beverages, ready to eat foods, food mix, feed mix, feed ingredients, food ingredients, gel, cream, ointment, spray, suppositories and the like.

The highly concentrated powdered oleoresin composition of the present invention can be used as flavoring agents in food items.

The highly concentrated powdered oleoresin composition of the present invention can be used in human, animal health and agricultural purpose.

The highly concentrated powdered oleoresin composition of the present invention has multiple benefits, such as higher stability, easy handling during manufacturing, ease of transportation, dose reduction due to higher concentration of oleoresins in nutraceutical and pharmaceuticals dosage forms, easy to formulate in the form of capsules or tablets with higher dose concentration of oleoresins and ease of blending with other ingredient without lumping problem.

Some typical examples illustrating the embodiments of the present invention are provided; however, these are exemplary only and should not be regarded as limiting the elements of the present invention.

EXAMPLES

Example 1: Composition for Preparation of Highly Concentrated Powdered Turmeric Oleoresins

| Sr. No. | Ingredients | Quantity (g) |
| --- | --- | --- |
| 1. | Turmeric Oleoresin | 82.67 |
| 2. | Propionic acid | 3.95 |
| 3. | MCC | 5.94 |
| 4. | Magnesium hydroxide | 6.44 |
| 5. | Silicon dioxide | 1 |
| | Total | 100 |

Example 2: HPLC Analysis Result of Curcuminoids in Turmeric Oleoresin Powder Composition Briefed in Example 1

| Sr. No. | Active | Assay value (%) |
| --- | --- | --- |
| 1. | Curcumin | 13.5 |
| 2. | Desmethoxycurcumin | 4.94 |
| 3. | Bis Desmethoxycurcumin | 4.08 |
| | Total Curcuminoid | 22.52 |

FIG. 1 represents the HPLC chromatogram for Turmeric oleoresin powder of composition of Example 1.

Example 3: Composition for Preparation of Highly Concentrated Powdered Turmeric Oleoresins

| Sr. No. | Ingredients | Quantity (g) |
| --- | --- | --- |
| 1. | Turmeric oleoresin | 81.90 |
| 2. | Citric acid | 3.90 |
| 3. | Magnesium hydroxide | 11.70 |
| 4. | Magnesium stearate | 0.5 |
| 5. | Silicon dioxide | 2 |
| | Total | 100 |

Example 4: HPLC Analysis Result of Curcuminoids in Turmeric Oleoresin Powder Composition Briefed in Example 3

| Active | Assay value (%) |
| --- | --- |
| Total Curcuminoid | 8.95 |

Example 5: Composition for Preparation of Highly Concentrated Powdered Turmeric Oleoresins

| Sr. No. | Ingredients | Quantity (g) |
| --- | --- | --- |
| 1. | Turmeric oleoresin | 81.34 |
| 2. | Propionic acid | 3.92 |
| 3. | Magnesium hydroxide | 6.86 |
| 4. | MCC | 5.88 |
| 5. | Silicon dioxide | 2 |
| | Total | 100 |

Example 6: HPLC Analysis Result of Curcuminoids in Turmeric Oleoresin Powder Composition Briefed in Example 5

| Active | Assay value (%) |
| --- | --- |
| Total Curcuminoid | 26.23 |

Figure 2:
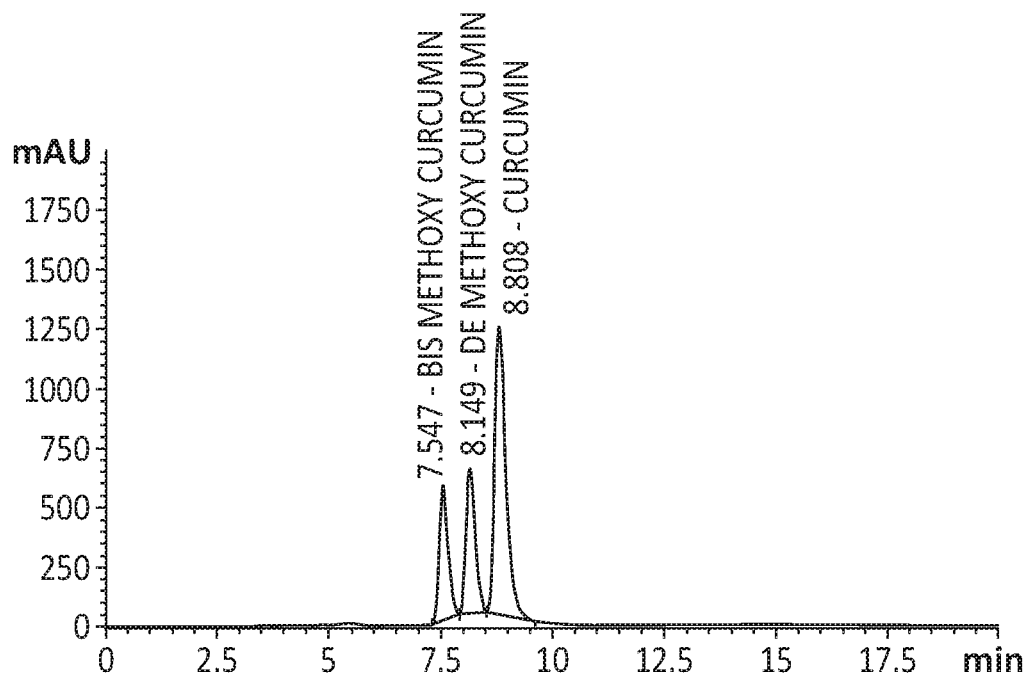
FIG. 2 represents the HPLC chromatogram for Turmeric oleoresin powder of composition of Example 5.

FIG. 2 represents the HPLC chromatogram for Turmeric oleoresin powder of composition of Example 5.

Example 7: Composition for Preparation of Highly Concentrated Powdered Turmeric Oleoresin

| Sr. No. | Ingredients | Quantity (g) |
| --- | --- | --- |
| 1. | Turmeric oleoresin | 30 |
| 2. | Magnesium hydroxide | 5 |
| 3. | Propionic acid | 2 |
| 4. | MCC | 61 |
| 5. | Silicon dioxide | 2 |
| | Total | 100 |

Example 8: Composition for Preparation of Highly Concentrated Powdered Turmeric Oleoresin

| Sr. No. | Ingredients | Quantity (g) |
| --- | --- | --- |
| 1. | Turmeric oleoresin | 40 |
| 2. | Magnesium hydroxide | 30 |
| 3. | Propionic acid | 20 |
| 4. | MCC | 8 |
| 5. | Silicon dioxide | 2 |
| | Total | 100 |

Example 9: Composition for Preparation of Highly Concentrated Powdered Turmeric Oleoresin

| Sr. No. | Ingredients | Quantity (g) |
| --- | --- | --- |
| 1. | Turmeric oleoresin | 90 |
| 2. | Magnesium hydroxide | 7.5 |
| 3. | Propionic acid | 2 |
| 4. | Silicon dioxide | 0.5 |
| | Total | 100 |

Example 10: Composition for Preparation of Highly Concentrated Powdered Turmeric Oleoresin

| Sr. No. | Ingredients | Quantity (g) |
| --- | --- | --- |
| 1. | Turmeric oleoresin | 90 |
| 2. | Calcium hydroxide | 6 |
| 3. | MCC | 3.5 |
| 4. | Silicon dioxide | 0.5 |
| | Total | 100 |

Example 11: Comparison of Solubility of Powdered Turmeric Oleoresin Composition of Example 1 with Unformulated Turmeric Oleoresin

| Sl. No. | Properties | Unformulated Curcuminoid Oleoresin | Formulated Curcuminoid Oleoresin of Example 1 |
| --- | --- | --- | --- |
| 1. | Physical nature | Thick sticky liquid | Free flowing powder |
| 2. | Solubility in water & Bioavailability | Nil | Soluble in water; Bioavailable |
| 3. | Ease of handling | Difficult to handle | Easy to handle |

Figure 3:
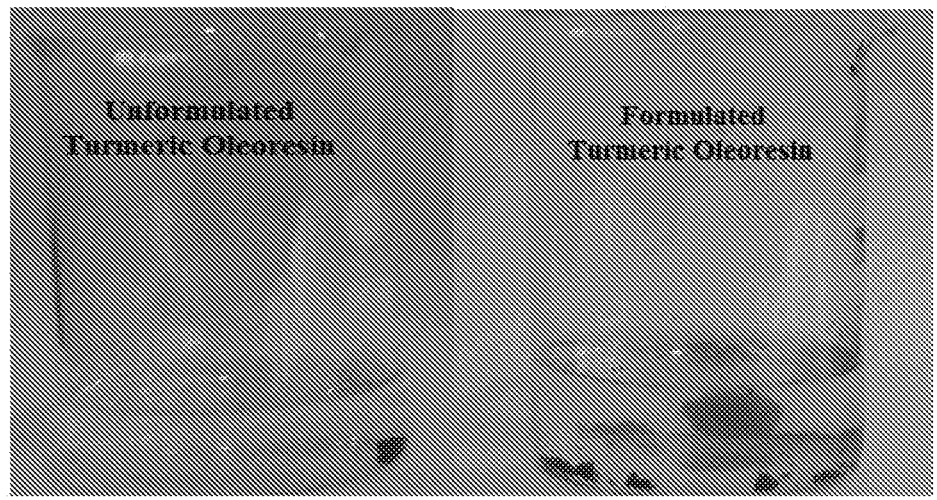
FIG. 3 represents the Solubility comparison of unformulated turmeric oleoresin with formulated powdered Turmeric Oleoresin of Example 1.

FIG. 3 represents the Solubility comparison of unformulated turmeric oleoresin with formulated Powdered Turmeric Oleoresin of Example 1. Solubility of the active ingredient indicates the higher bioavailability. If the solubility is enhanced/higher, then bioavailability will be increased. The light yellow colour solution of formulated Turmeric Oleoresin in FIG. 3 indicates higher solubility of Curcuminoids from powdered oleoresin product. Hence, FIG. 3 clearly exhibits that the Curcuminoids from powdered oleoresin product has higher bioavailability than unformulated turmeric oleoresin.

Example 12

Process for preparation of highly concentrated powdered Turmeric oleoresins composition (with organic/inorganic acid) comprises the following steps:
 a) Cleaning the reactors fitted with stirrer;
 b) adding Turmeric oleoresin to the reactor of step (a);
 c) adding propionic acid to step (b) followed by blending;
 d) adding Magnesium/calcium hydroxide to step (c) at the temperature range of 25 to 80° C. followed by blending/mixing for 10 to 30 minutes;
 e) transferring the mixture of step (d) in to Stainless Steel tray and allowing it to become dry for 1 to 24 hrs.;
 f) powdering the hard mixture of step (e) into free flowing powder;
 g) optionally adding MCC (microcrystalline cellulose) and silicon dioxide to step (f); and
 h) sieving and packing of the obtained product.

Example 13

Process for preparation of highly concentrated powdered Turmeric oleoresins composition (without organic/inorganic acid) comprises the following steps:
 a) Cleaning the reactors fitted with stirrer;
 b) adding Turmeric oleoresin to the reactor of step (a);
 c) adding Magnesium/calcium hydroxide to step (b) at the temperature range of 25 to 80° C., followed by blending/mixing for 10 to 30 minutes;
 d) transferring the mixture of step (c) in to Stainless Steel tray and allowing it to become dry for 1 to 24 hrs.;
 e) powdering the hard mixture of step (d) into free flowing powder;
 f) optionally adding MCC (microcrystalline cellulose) and silicon dioxide to step (e); and
 g) sieving and packing of the obtained product.

Example 14: Composition for Preparation of Highly Concentrated Powdered Marigold Oleoresins

| Sr. No. | Ingredients | Quantity (g) |
| --- | --- | --- |
| 1. | Marigold oleoresin | 75 |
| 2. | Propionic acid | 5 |
| 3. | Potassium hydroxide | 14 |
| 4. | MCC | 4 |
| 5. | Silicon dioxide | 2 |
|  | Total | 100 |

Example 15: Composition for Preparation of Highly Concentrated Powdered Marigold Oleoresins

| Sr. No. | Ingredients | Quantity (g) |
| --- | --- | --- |
| 1. | Marigold oleoresin | 75 |
| 2. | Citric acid | 5 |
| 3. | Potassium hydroxide | 14 |
| 4. | MCC | 4 |
| 5. | Silicon dioxide | 2 |
|  | Total | 100 |

Example 16: Composition for Preparation of Highly Concentrated Powdered Fenugreek Oleoresins

| Sr. No. | Ingredients | Quantity (g) |
| --- | --- | --- |
| 1. | Fenugreek oleoresin | 85 |
| 2. | Citric acid | 4 |
| 3. | Calcium Hydroxide | 11 |
|  | Total | 100 |

Example 17: Composition for Preparation of Highly Concentrated Powdered Fenugreek Oleoresins

| Sr. No. | Ingredients | Quantity (g) |
| --- | --- | --- |
| 1. | Fenugreek oleoresin | 85 |
| 2. | Citric acid | 4 |
| 3. | Magnesium Hydroxide | 11 |
|  | Total | 100 |

Example 18: Composition for Preparation of Highly Concentrated Powdered Cinnamon Oleoresin

| Sr. No. | Ingredients | Quantity (g) |
| --- | --- | --- |
| 1. | Cinnamon oleoresin | 80 |
| 2. | Magnesium hydroxide | 12 |
| 3. | MCC | 6 |
| 4. | Silicon dioxide | 2 |
|  | Total | 100 |

Example 19: Composition for Preparation of Highly Concentrated Powdered Nutmeg Oleoresin

| Sr. No. | Ingredients | Quantity (g) |
| --- | --- | --- |
| 1. | Nutmeg oleoresin | 70 |
| 2. | Calcium hydroxide | 12 |
| 3. | Citric acid | 7 |
| 4. | MCC | 9 |
| 5. | Silicon dioxide | 2 |
|  | Total | 100 |

Example 20: Composition for Preparation of Highly Concentrated Powdered Paprika Oleoresin

| Sr. No. | Ingredients | Quantity (g) |
| --- | --- | --- |
| 1. | Paprika oleoresin | 75 |
| 2. | Magnesium hydroxide | 8 |
| 3. | Acetic acid | 7 |
| 4. | MCC | 8 |
| 5. | Silicon dioxide | 2 |
|  | Total | 100 |

Example 21: Composition for Preparation of Highly Concentrated Powdered Capsicum Oleoresin

| Sr. No. | Ingredients | Quantity (g) |
| --- | --- | --- |
| 1. | Capsicum oleoresin | 75 |
| 2. | Magnesium hydroxide | 15 |
| 3. | MCC | 8 |
| 4. | Silicon dioxide | 2 |
|  | Total | 100 |

Example 22: Composition for Preparation of Highly Concentrated Powdered Ginger Oleoresin

| Sr. No. | Ingredients | Quantity (g) |
| --- | --- | --- |
| 1. | Ginger oleoresin extract | 86.28 |
| 2. | MCC | 1.96 |

-continued

| Sr. No. | Ingredients | Quantity (g) |
|---|---|---|
| 3. | Calcium Hydroxide | 9.80 |
| 4. | Silicon dioxide | 1.96 |
| | Total | 100 |

Example 23: HPLC Analysis Results of Gingerol Oleoresin Powder Composition Briefed in Example 22

| Active | Assay value (%) |
|---|---|
| Total pungent compounds | 24.3 |

Figure 4:
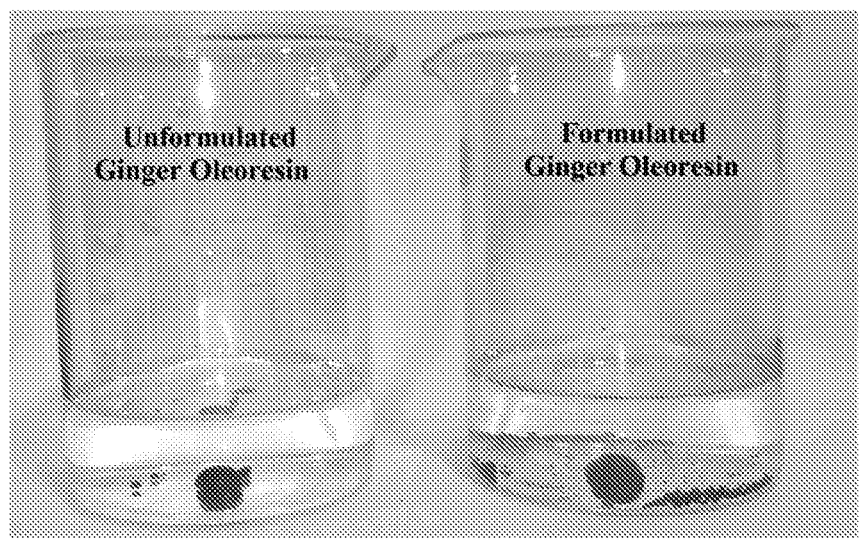
FIG. 4 represents the Solubility comparison of unformulated ginger oleoresin with formulated powdered ginger Oleoresin of Example 22.

FIG. 4 represents the Solubility comparison of unformulated ginger oleoresin with formulated powdered ginger Oleoresin of Example 22. Solubility of the active ingredient indicates the higher bioavailability. If the solubility is enhanced/higher, then bioavailability will be increased. The light yellow colour solution of formulated ginger Oleoresin in FIG. 4 indicates the higher solubility of the gingerol from powdered oleoresin product. Hence, FIG. 4 clearly exhibits that the gingerol from powdered oleoresin product has higher bioavailability than unformulated ginger oleoresin.

Example 24: Composition for Preparation of Highly Concentrated Powdered Ginger Oleoresin

| Sr. No. | Ingredients | Quantity (g) |
|---|---|---|
| 1. | Ginger Oleoresin extract | 71.81 |
| 2. | Citric acid | 1.67 |
| 3. | Calcium Hydroxide | 10.02 |
| 4. | MCC | 16 |
| 5. | Magnesium stearate | 0.5 |
| | Total | 100 |

Example 26: Comparison of Powdered Ginger Oleoresin Composition of Example 22 with Marketed (Microencapsulated) Products and Evidence for Higher Concentration of Actives in the Composition of Current Invention

| Parameters | Assay/ Name of the Actives | Percentage active concentration in Composition of Example 22 | Percentage active concentration in Marketed Product (Microencapsulated) |
|---|---|---|---|
| Physical state | — | Free flowing Powder | Free flowing Powder |
| Active ingredient (%) | % Gingerol content | >24% total Gingerol | 5% total Gingerol |
| Ginger Oleoresin content | % Ginger Oleoresin content | >80% | 12.5% |

Example 27: Comparison of Formulated Powdered Ginger Oleoresin Composition of Example 22 and Unformulated Ginger Oleoresin

| Sl. No. | Properties | Unformulated Ginger Oleoresin | Formulated Ginger Oleoresin of Example 22 |
|---|---|---|---|
| 1. | Physical nature | Thick sticky liquid | Free flowing powder |
| 2. | Solubility in water | Nil | Soluble in water |
| 3. | Ease of handling | Difficult to handle | Easy to handle |

Example 28

Process for preparation of highly concentrated powdered Ginger oleoresins composition (with organic/inorganic acid) comprises the following steps:
a) Cleaning the reactors fitted with stirrer;
b) heating Ginger oleoresin to the temperature between 25 to 50° C.;
c) adding citric acid to step (b) followed by blending;
d) adding Calcium Hydroxide to step (c) followed by blending/mixing for 10 to 30 minutes;
e) transferring the mixture of step (d) in to Stainless Steel tray and allowing it to become dry for 1 to 24 hrs.;
f) powdering the hard mixture of step (e) into free flowing powder;
g) adding MCC (microcrystalline cellulose) and silicon dioxide to step (f); and
h) sieving and packing of the obtained product.

Example 29

Process for preparation of highly concentrated powdered Ginger oleoresins composition (without organic/inorganic acid) comprises the following steps:
a) Cleaning the reactors fitted with stirrer;
b) adding Ginger oleoresin to the reactor of step (a) followed by heating;
c) adding Calcium hydroxide at the temperature range of 25 to 50° C. followed by blending/mixing for 10 to 30 minutes;
d) transferring the mixture of step (c) in to Stainless Steel tray and allowing it to become dry for 1 to 24 hrs.;
e) powdering the hard mixture of step (d) into free flowing powder;
f) adding MCC (microcrystalline cellulose) and silicon dioxide to step (e) and
g) sieving and packing of the obtained product.

Example 30: Comparative Stability Study Data of Turmeric Oleoresin Unformulated Liquid with Formulated Powder

| SL. No. | Time Period | Unformulated Liquid Turmeric Oleoresin | Formulated Powder Turmeric Oleoresin of Example 1 |
|---|---|---|---|
| 1. | Initial | 33.6% | 22.56% |
| 2. | $1^{st}$ month | 31.45% | 22.4% |
| 3. | $3^{rd}$ month | 29.2% | 22.36% |
| 4. | $6^{th}$ month | 26.32% | 22.26% |

We claim:

1. A tablet or capsule consisting essentially of:
an oleoresin selected from the group consisting of a clove oleoresin, a curry leaf oleoresin, a pepper oleoresin, a cardamom oleoresin, a chili oleoresin, a capsicum oleoresin, a paprika oleoresin, a ginger oleoresin, a *curcuma xanthorrhiza* oleoresin, a turmeric oleoresin, a coriander oleoresin, a cumin oleoresin, a celery oleoresin, a dill oleoresin, a fenugreek oleoresin, a garlic oleoresin, a mace oleoresin, a garcinia extract, a fennel oleoresin, a tamarind oleoresin, a cinnamon oleoresin, a nutmeg oleoresin, a cassia oleoresin, a galangal oleoresin, a parsley oleoresin, a thyme oleoresin, a marigold oleoresin, a rosemary oleoresin, a mustard oleoresin, a curry powder oleoresin, a vanilla oleoresin, and mixtures thereof;
a first compound selected from the group consisting of calcium hydroxide, magnesium hydroxide, zinc hydroxide, iron hydroxide, aluminium hydroxide, selenium hydroxide, sodium hydroxide, potassium hydroxide, calcium oxide, magnesium oxide, zinc oxide, iron oxide, selenium oxide, potassium oxide, magnesium chloride, and mixtures thereof;
a second compound selected from the group consisting of propionic acid, formic acid, acetic acid, citric acid, butyric acid, valeric acid, caproic acid, oxalic acid, lactic acid, malic acid, phosphoric acid, benzoic acid, carbonic acid, and mixtures thereof; and
microcrystalline cellulose.

2. A tablet or capsule consisting essentially of:
an oleoresin selected from the group consisting of a clove oleoresin, a curry leaf oleoresin, a pepper oleoresin, a cardamom oleoresin, a chili oleoresin, a capsicum oleoresin, a paprika oleoresin, a ginger oleoresin, a *curcuma xanthorrhiza* oleoresin, a turmeric oleoresin, a coriander oleoresin, a cumin oleoresin, a celery oleoresin, a dill oleoresin, a fenugreek oleoresin, a garlic oleoresin, a mace oleoresin, a garcinia extract, a fennel oleoresin, a tamarind oleoresin, a cinnamon oleoresin, a nutmeg oleoresin, a cassia oleoresin, a galangal oleoresin, a parsley oleoresin, a thyme oleoresin, a marigold oleoresin, a rosemary oleoresin, a mustard oleoresin, a curry powder oleoresin, a vanilla oleoresin, and mixtures thereof;
a first compound selected from the group consisting of calcium hydroxide, magnesium hydroxide, zinc hydroxide, iron hydroxide, aluminium hydroxide, selenium hydroxide, sodium hydroxide, potassium hydroxide, calcium oxide, magnesium oxide, zinc oxide, iron oxide, selenium oxide, potassium oxide, magnesium chloride, and mixtures thereof;
a second compound selected from the group consisting of propionic acid, formic acid, acetic acid, citric acid, butyric acid, valeric acid, caproic acid, oxalic acid, lactic acid, malic acid, phosphoric acid, benzoic acid, carbonic acid, and mixtures thereof;
microcrystalline cellulose; and
silicon dioxide.

* * * * *